United States Patent
Schlotawa et al.

(10) Patent No.: US 11,696,897 B2
(45) Date of Patent: Jul. 11, 2023

(54) METHOD FOR THE TREATMENT OF DISEASES ASSOCIATED WITH SULFATASE DEFICIENCIES

(71) Applicants: GEORG-AUGUST-UNIVERSITAT GOTTINGEN STIFTUNG OFFENTLICHEN RECHTS, UNIVERSITATSMEDIZIN, Gottingen (DE); UNIVERSITAT BIELEFELD, Bielefeld (DE)

(72) Inventors: Lars Schlotawa, Gottingen (DE); Matthias Kettwig, Gottingen (DE); Karthikeyan Radhakrishnan, Bielefeld (DE); Thomas Dierks, Bielefeld (DE); Jutta Gartner, Gottingen (DE); Matthias Baud, Southampton (GB)

(73) Assignee: GEORG-AUGUST-UNIVERSITAT GOTTINGEN STIFTUNG OFFENTLICHEN RECHTS, UNIVERSITATSMEDIZIN, Gottingen (DE)

(*) Notice: Subject to any disclaimer, the term of this patent is extended or adjusted under 35 U.S.C. 154(b) by 2 days.

(21) Appl. No.: 16/591,051

(22) Filed: Oct. 2, 2019

(65) Prior Publication Data
US 2021/0100756 A1    Apr. 8, 2021

(51) Int. Cl.
*A61K 31/07* (2006.01)
*A61P 3/00* (2006.01)
*A61K 31/44* (2006.01)

(52) U.S. Cl.
CPC ............... *A61K 31/07* (2013.01); *A61P 3/00* (2018.01)

(58) Field of Classification Search
CPC ............ A61K 31/07; A61K 31/44; A61P 3/00
See application file for complete search history.

(56) References Cited

PUBLICATIONS

Anderson, Chemistry & Biology 2003, vol. 10, pp. 787-797. (Year: 2003).*
Thiel, Nature Biotechnology 2004, vol. 22, No. 5, pp. 513-519. (Year: 2004).*
Panthagani et al, DermNet NZ (2005), pp. 1-5. (Year: 2005).*
Azulay et al, Daily Routine in Cosmetic Dermatology 2016, pp. 1-16. (Year: 2016).*
Ferreira et al, Nature Communications 2020, pp. 1-14. (Year: 2020).*
Azulay et al, "Retinoids" Daily Routine in Cosmetic Dermatology 2016, pp. 1-16. (Year: 2016).*
Vahlquist et al. Acta Derm Venereol 2008, vol. 88, pp. 4-14 (Year: 2008).*

* cited by examiner

*Primary Examiner* — Craig D Ricci
*Assistant Examiner* — Janet L Coppins
(74) *Attorney, Agent, or Firm* — WC&F IP (57) ABSTRACT

A method for a treatment of individuals suffering from diseases associated with sulfatase deficiencies including lysosomal storage disease includes administering at least once a therapeutically effective amount of at least one retinoid. In particular, the compounds tazaroten and bexaroten have beneficial effects on these individuals. Pharmaceutical compositions comprising both active agents namely, tazaroten and bexaroten compounds, or similar compounds, provides for ready treatment of such individuals, and enhanced treatment is achieved with at least two active agents.

6 Claims, 6 Drawing Sheets

METHOD FOR THE TREATMENT OF DISEASES ASSOCIATED WITH SULFATASE DEFICIENCIES

FIELD OF THE INVENTION

The present invention relates in a first aspect to a method for a treatment of individuals suffering from diseases associated with sulfatase deficiencies including lysosomal storage disease comprising the step of administering at least once a therapeutically effective amount of at least one retinoid to said individual. In particular, the present inventors recognized that compounds tazaroten and bexaroten have beneficial effects on said individuals. In a further aspect, a pharmaceutical composition comprising both active agents namely, tazaroten and bexaroten compound or similar compounds is provided. In addition, the present invention relates to the treatment of individuals with said pharmaceutical composition containing at least two active agents.

BACKGROUND

Multiple sulfatase deficiency (MSD; MIM #272200) is a rare inherited autosomal recessive metabolic disease. The prevalence is 1:1,4 million newborn, actually more than fifty patients are known to suffer from said disease. MSD is caused by mutations in the SUMF1 gene. SUMF1 encodes the so called formylglycine-generating enzyme (FGE) a glycoprotein composed of 374 amino acids and located in the endoplasmatic reticulum. FGE posttranslationally activates newly synthesized sulfatases. Sulfatases are recognized by FGE based on conserved amino acid sequence (CTPSR) present in the active center of every sulfatase. FGE oxidizes the amino acid cysteine present in the above sequence to formylglycine, an aldehyde that is required for the catalytic activity of sulfatases. Mutations in the SUMF1 gene are the cause of a functional deficiency of FGE resulting in a limited activity and stability with the consequence of functional limitation of all cellular sulfatases. In particular, missense mutations as a type of hypomorphic mutations, which are the most frequent mutations in patients with MSD, have a low residual activity and stability of FGE.

The human genome contains seventeen genes encoding sulfatases which are activated by FGE. Most of these sulfatases are localized in the lysosomes, thus, a loss of activity of these sulfatases results in accumulation of lysosomal substrates and pathology of lysosomes. Other sulfatases are present at different locations in the cell, namely, endoplasmatic reticulum, golgi, cell surface, and are required for the desulfation of sulfated macro-molecules e.g. during signal transduction processes. The function of some of the sulfatases activated by FGE are yet unknown.

Lysosomal storage diseases (LSD), are a group of more than 50 rare inherited metabolic disorders that result from defects of lysosomal function. LSDs are usually caused as a consequence of deficiency of a single enzyme required for the metabolism of lipids, glycoproteins or so-called mucopolysaccharides. Most of these disorders are autosomal recessively inherited, examples include Niemann-Pick disease, type C, but a few are X-linked recessively inherited, such as Fabry disease and Hunter syndrome. Like other genetic disorders, individuals inherit lysosomal storage diseases from their parents. Although each disorder results from different gene mutations that translate into a deficiency in enzyme activity, they all share a biochemical characteristic; all lysosomal disorders originate form an abnormal accumulation of substances inside the lysosomes. LSDs mostly affect children and they often die at a young age, many within a few months or years after birth. There is a standard classification of LSDs generally classified by the nature of the primary stored material involved, mucopolycaccharidosis, sphingolipidosis, and oligosaccharidosis.

At present treatment options for lysosomal storage diseases are limited and are mostly restricted to treating the symptoms although bone marrow transplantation and enzyme replacement therapy have been tried with some success. For MSD the symptoms commonly appear between one or two years of age, some patients show neonatal onset, few a so called juvenile form with onset after two years. The disease is fatal, with symptoms that include neurological damage and severe mental retardation. Because most of the sulfatases are localized in lysosomes and corresponding loss of activity in this organelle, the clinical symptoms are a combination of single lysosomal sulfatase defects as well as lysosomal storage disease affecting a multitude of organ systems. The clinical syndromes are diverse: development delay and a mental retardation, neurologic symptoms and neurodegeneration, impaired vision and hearing, dysmorphia, growth disturbance and skeletal changes as well as skin diseases among others. MSD is divided into severe and attenuated form of disease based on single symptoms. The severity and characteristics of the disease depend on the severity and consequences of the respective SUMF1 mutation:

Mutations showing higher residual FGE activity, mostly result in stable variants of FGE, which in turn results in attenuated progression of the disease, whereas mutations causing instable FGE with low residual enzymatic activity cause severe MSD cases. Fifty percent of MSD patients die before the age of twelve, only few patients live longer than 20 years of age.

Until today no treatment for MSD exists, the therapeutic approaches are limited to the control of symptoms like antiepileptic therapy, physiotherapy, and ventilation. No therapy influences the progressive course of MSD over time.

Recently, gene therapy has been considered as a promising approach for the treatment of MSD and other sulfatase deficiencies as well as other lysosomal disorders. However, treatment of all effected organs systems in MSD requires large amounts of vector to be produced. Currently, only intrathecal administration of gene therapy for MSD is tested in animal models.

Retinoids are chemical derivatives of vitamin A. There are presently three generations of retinoids synthetically developed, which are more apart from the starting material. All retinoid bind to nuclear receptors that induce the transcription of depending genes respectively. Retinoid receptors comprise RAR-retinonid receptors and RXR-retinoid receptors. Retinoids bind with different affinity and selectivity to the respective receptors. After ligand binding, receptors of either group heterodimerize, and bind to a conserved DNA promoter sequence initiating the transcription of the respective genes.

Retinoids are typically used as therapy for skin diseases like psoriasis and acne. They are administered topically or systematically. Retinoids are well tolerated, however, undesired side effects may occur with these groups of compounds having a teratogenic potential, which is lower in the group of RXR active substances. Former work on lysosomal function describe that retinoid acid, a retinoid of the first generation, exhibits high affinity binding to the mannose-6-phosphate receptor at binding sites different to mannose-6 phosphate binding sites. Retinoic acid binding results in uptake of mannose-6 phosphate bound lysosomal hydrolases by endocytosis and intracellular accumulation in cytoplasmic vesicles. Interestingly, retinoic acid mediated endocytosis could not be prevented by blocking retinoid acid receptors and treatment with selective retinoid receptor agonists did not show the same results. Thus, a retinoid receptor independent mechanism of retinoid acid binding to mannose-6 phosphate receptors has been postulated with influence on the intracellular trafficing of lysosomal hydrolases.

SUMMARY

In a first aspect, the present invention relates to a method for the treatment of individuals suffering from diseases associated with sulfatase deficiencies including lysosomal storage diseases comprising the step of administering at least once a therapeutically effective amount of at least one retinoid to said individual. In a preferred embodiment, this retinoid is at least one of the retinoid of the compound of the formula I.

where X is S or O; R is hydrogen or C1-C4 alkyl; $R_2$ is methyl; A is pyridyl; n is 0-2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or disubstituted amide thereof, the substituents on the amide being selected from a group consisting of saturated aliphatic radicals of ten or fewer carbon atoms, cyclic or saturated aliphatic cyclic radicals of 5 to 10 carbon atoms, and phenyl or C1-C4 alkylphenyl radicals.

In another aspect, the at least one retinoid is a compound of formula II wherein $R_1$, $R_2$, $R_3$ and $R_4$ each independently represent hydrogen or lower alkyl having 1-4 carbon atoms; Y represents C, O, S, N;

$R_5$ represents hydrogen, a lower alkyl having 1-4 carbon atoms, halogen, or nitro;

$R_6$ represents hydrogen, a lower alkyl having 1-4 carbon atoms, halogen, or nitro;

$R_7$ and $R_8$ each independently represent hydrogen or lower alkyl having 1-4 carbon atoms;

$R_9$ is COOH, CHO, $CH_2OH$, $CONH_2$, COSH, $COOR_{10}$, $COSR_{10}$, $CONHR_{10}$ with $R_{10}$ represents a lower alkyl having 1-4 carbons or a pharmaceutically acceptable salt thereof.

In particular, it is preferred that the at least one retinoid is selected from tazaroten and bexarotene.

In a further aspect, the present invention relates to a pharmaceutical composition comprising a combination of at least two agents on retinoid basis when at least one active agent is a compound of general formula I and the second retinoid based active compound is a compound of general formula II. Moreover, the present invention relates to a method for the treatment of individuals suffering from diseases associated with sulfatase deficiencies including the treatment of individuals suffering from lysosomal storage diseases comprising administering the pharmaceutical composition according to the present invention.

DESCRIPTION OF THE DRAWINGS

In FIG. 6 3d incubation of immortalized MSD with bexarotene is shown.

DETAILED DESCRIPTION

The present invention relates in a first aspect to a method for the treatment of individuals suffering from diseases associated with sulfatase deficiencies including individuals suffering from lysosomal storage diseases comprising a step of administering at least once a therapeutically effective amount of at least one retinoid to said individual.

As used herein, the term "diseases associated with sulfatase deficiencies" refers to diseases deriving from dysfunction of sulfatases encoded in cells of an individual. Dysfunction comprises not only a reduced activity of the enzyme itself, but in general circumstances, which reduce the sulfatase performance in cells. Such circumstances reducing the performance of the sulfatase in cells include interaction with other proteins or binding partners, a misallocation or reduced cellular concentrations of the sulfatase. Examples of sulfatases effected are shown in table 1.

TABLE 1

Multiple sulfatase deficiency affects 17 unique sulfatases, each with distinct subcellular localizations and pathogenic associations.

| Subcellular localization | Sulfatase | Disease |
|---|---|---|
| Lysosome | Arylsulfatase A (Cerebroside-3-sulfatase) | Metachromatic Leukodystrophy (MIM 250100) |
| | Arylsulfatase B (N-Acetyl-Galactosamine-4-Sulfatase) | MPS VI Maroteaux-Lamy (MIM 253200) |
| | Iduronate-2-Sulfatase | MPS 11 Hunter (MIM 309900) |
| | Sulfamidase (N-Sulfoglucosamine-Sulfohydrolase) | MPS IIIA Sanfilippo (MIM 252900) |

TABLE 1-continued

Multiple sulfatase deficiency affects 17 unique sulfatases, each with distinct subcellular localizations and pathogenic associations.

| Subcellular localization | Sulfatase | Disease |
| --- | --- | --- |
| | N-Acetylglucosamine-6-Sulfatase | MPS IIID Sanfilippo IIID (MIM 252940) |
| | Galactosamine-6-Sulfatase | MPS IVA Morquio A (MIM 253000) |
| | Arylsulfatase G (N-Sulfoglucosamine-3-sulfatase) | Usher Syndrome Type IV (MIM 618144) |
| | Arylsulfatase K (Glucuronate-2-sulfatase) (82) | unknown |
| Endoplasmic Reticulum | Arylsulfatase C (Steroid Sulfatase) | X-linked Ichthyosis (MIM 308100) |
| | Arylsulfatase D | unknown |
| | Arylsulfatase F | unknown |
| Cell surface | Sulfatase 1 | unknown |
| Brian Bigger questioned this from Dierks's paper- he thinks ER. I will send a picture of the paper he marked for me at Worlds 2017 | Sulfatase 2 | unknown |
| Golgi | Arylsulfatase E | Chondrodysplasia punctata Type I (MIM 302950) |
| Unknown | Arylsulfatase H | unknown |
| | Arylsulfatase I | unknown |
| | Arylsulfatase J | unknown |

The present inventors recognized that surprisingly retinoid compounds have an influence, namely, increase the activity of sulfatases, which is reduced in diseases associated with sulfatase deficiencies exemplified by multiple sulfatase deficiency (MSD). In an embodiment, the individual is a human.

In an embodiment of the present invention, the therapeutically effective amount of at least one retinoid administered to said individual is periodically repeated. For example, administration may be daily, more than one time per day but also weekly, monthly or systemically by implant etc.

In a further aspect, the retinoid is a retinoid of the third generation. The skilled person is well aware of retinoid derivatives falling under the definition of third generational retinoids.

In a particular embodiment, the method for treatment of individuals according to the present invention includes administration of at least one retinoid being a compound of the formula I where X is S or O; R is hydrogen or lower alkyl having 1 to 4 carbon atoms $R_2$ is methyl; A is pyridyl; n is 0-2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or disubstituted amide thereof, the substituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals.

Compounds of the general formula I are described for example in U.S. Pat. No. 5,089,509 which is incorporated herein fully.

The compound of general formula I is for example a compound wherein X is S, R is hydrogen, and n is 0 or 1. Particularly, the compound of general formula I is tazarotene also known as ethyl 6-(2-(4,4-dimethylthiochroman-6-yl) ethynyl)nicotinate.

The retinoid compounds administered in the method according to the present invention maybe in the form as they are or maybe in form of a pharmaceutical acceptable salt or hydrate thereof. The skilled person is well aware of suitable forms of the retinoid allowing administration to an individual accordingly.

In another aspect, the present invention refers to the method for treatment of individuals as described herein including treatment of individuals suffering from diseases associated with sulfatase deficiencies as well as treatment of individuals suffering from lysosomal storage diseases, wherein the at least one retinoid is a compound of general formula II wherein $R_1$, $R_2$, $R_3$ and $R_4$ each independently represent hydrogen or lower alkyl having 1-4 carbon atoms;

Y represents C, O, S, N;

$R_5$ represents hydrogen, a lower alkyl having 1-4 carbons, halogen, or nitro;

$R_6$ represents hydrogen, a lower alkyl having 1-4 carbons, halogen, or nitro;

$R_7$ and $R_8$ each independently represent hydrogen or lower alkyl having 1-4 carbon atoms;

$R_9$ is COOH, CHO, $CH_2OH$, $CONH_2$, COSH, $COOR_{10}$, $COSR_{10}$, $CONHR_{10}$ with $R_{10}$ represents a lower alkyl having 1-4 carbons or a pharmaceutically acceptable salt thereof.

As used herein, the term "lower" alkyl refer to alkyl residues having C1 to C4 carbon atoms. The term include the embodiments of C1 alkyl, C2 alkyl, C3 alkyl and C4 alkyl.

A preferred embodiment of the compound of general formula II is the retinoid 4-[1-(5,6,7,8-tetrahydro-3,5,5,8,8-pentamethyl-2-naphthalenyl)ethenyl]benzoic acid, also known as bexarotene. So far bexarotene is known for various purposes including and topical treatment of cutaneous lesions and patients with CTCL off-labels described in a non-small cell cancer and breast cancer. That is, bexarotene is known for treatment of various cancer diseases.

Compounds of the general formula II are described for example in U.S. Pat. No. 5,780,878 which is incorporated herein fully.

Tazarotene is one of the retinoid compounds administered in the method according to present invention is described in the treatment of skin diseases including acne and psoriasis as well as in reducing skin tingling and liver spots. Other uses are not described so far.

Surprisingly, the present inventors recognized that e.g. tazarotene as well as bexarotene have beneficial effects on sulfatase activity in MSD cells as a model for MSD. As demonstrated below, administering pharmaceutical effective amounts of tazarotene or bexarotene results in increasing the activity of arylsulfatase A and other sulfatases activity known to be reduced in MSD patients.

In particular, administration of a combination of both allows to increase activity reproducibly and remarkably while the single dosage of each of the compounds can be reduced. By this means, it is possible to reduce single dosages of each of the compounds, thus, decreasing the described side effects of tazarotene and bexarotene respectively.

The administration may be effected through oral or intravenous treatment; other routes of administration (topical or subcutaneous) are possible. Of course, it is possible that when administering a combination of at least two retinoids, the way of administration will be identical or different.

The administration of the combination of at least retinoids according to the present invention may be effected simultaneously, sequentially or subsequently. The skilled person is well aware of the suitable way, dosage and time of administration. In an embodiment, the administration of the first component may be systemically, while the second component may be administered orally or vice versa.

The diseases involving sulfatase deficiencies include metachromatic leukodystrophy (MIM #250100), MPSII (MIM #309900), MPSIIIa (MIM #252900), MPS IIId (MIM #252940), MPS IVa (MIM 253000), MPS VI (MIM #253200), chondrodysplasia punctata I (MIM #302950), Usher syndrome (MIM #618144) and X-linked Ichthyosis (MIM #308100) as well as yet undescribed diseases due to deficiencies of arylsulfatases D, H, I, J, K, and sulfatase 1 and 2. In particular, the sulfatase deficiency may be a multi sulfatase deficiency or a single sulfatase deficiency, e.g. as mentioned in table 1 above.

Further, the disease may be a lysosomal storage disease with sulfatase deficiencies.

In a preferred aspect of the present invention, the method for the treatment of individuals suffering from diseases associated with sulfatase deficiencies including lysosomal storage disease comprise the step of administering a therapeutically effective amount of a combination of ethyl 6-(2-(4,4-dimethylthiochroman-6-yl)ethynyl)nicotinate or a pharmaceutically acceptable salt thereof and 4-[1-(5,6,7,8-tetrahydro-3,5,5,8,8-pentamethyl-2-naphthalenyl)ethenyl]benzoic acid or a pharmaceutically acceptable salt thereof.

In another aspect of the present invention, the present invention relates to a pharmaceutical composition comprising a combination of at least two active agents on retinoid basis wherein at least one active agent is a compound of general formula I and the second retinoid based active compound is a compound of general formula II.

In an embodiment of this pharmaceutical composition, the pharmaceutical composition is a composition wherein the first active agent is ethyl 6-(2-(4,4-dimethylthiochroman-6-yl)ethynyl)nicotinate or a pharmaceutically acceptable salt thereof and the second active agent is 4-[1-(5,6,7,8-tetrahydro-3,5,5,8,8-pentamethyl-2-naphthalenyl)ethenyl]benzoic acid or a pharmaceutically acceptable salt thereof.

The pharmaceutical composition according to the present invention may comprise additional components including diluent, excipients or carrier. Suitable compounds are known to the skilled person. The pharmaceutical composition may be administered with a physiologically acceptable carrier to an individual. In a specific embodiment, the term "pharmaceutically accepted" means approved by regulatory agency or other generally recognized pharmacopoea for use in animals and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly, for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skin milk, glycerol, propylene glycol, water, ethanol and the like. The pharmaceutical composition, if desired, can also contain minor amounts of wetting or emulsifying agent, or pH buffering agents. These compositions can take the form of solutions, suspensions, emulsion, tablets, pills, capsules, powders, sustained-release formulations, patches and the like. The compositions will contain a therapeutically effective amount of the compounds according to the present invention, preferably in purified form, together with a suitable amount of carrier so as to provide the form for proper administration to the individual. The formulation should suit the mode of administration. The route of administration of the compounds of the present invention depends on the formulation in use. The composition is formulated in accordance with routine procedures as the pharmaceutical composition adapted for intravenous or oral administration to individuals including human beings. Typically, composition for intravenous administrations or solutions in sterile isotonic aqueous buffer.

The term "administered" means administration of therapeutically effective dose or dosage of the pharmaceutical composition or the compounds according to the present invention. The methods are applicable to both human therapy and veterinary applications. The administration of the pharmaceutical composition can be done in a physiologically acceptable carrier as discussed above, including, but not limiting to, orally, subcutaneously, intravenously, intraarterially, intraorally, intramedullary, intrathecally, intraventicularly, intranasally, intrabronchially, transdermally, intrarectally, intraperitoneally, intramuscularly, intrapulmonarily, vaginally, rectally, or intraoculary. Effective doses may be extrapolated from dose-response curves derived from in vitro animal model tests. As it is known in the art and described herein, adjustments for systemic versus locally delivery, age, body weight, generally health, sex, diet, time of administration, drug interaction and the severity of the condition may be necessary, and will be ascertainable with routine experimentation by those skilled in the art.

In an embodiment of the present invention, the compounds according to the present invention are the only pharmaceutical active agent comprised in said pharmaceutical composition. In case where more than one active agent is present in the pharmaceutical composition, the pharmaceutical composition may be adapted for allowing simultaneous, separate or sequential administration of the different active agents.

Moreover, the present invention relates to a method for the treatment of individuals suffering from diseases associated with sulfatase deficiencies comprising the administration of a pharmaceutical composition according to the present invention. Administration may be conducted simultaneously, sequentially or subsequently.

The present invention will be described further by way of example without limiting the present invention.

EXAMPLE

In a first step, suitable substances useful in the treatment of MSD were screened. Namely, based in an enzymatic activity assay measuring the activity of aryl sulfatase A, a sulfatase showing a reduced activity in MSD patient in human fibroblasts has been developed. The cell line used is a spontaneously immortalized MSD fibroblast cell line (MSDi) showing a high in vitro growth rate (Cosma et al. Cell, Vol 113, 445-456, May 16, 2003).

The assay allows to screen a large number of compounds which may be suitable candidates for treating MSD. The final concentration of the candidate compounds screened in the described assay is about 10 μM in the supernatant on the human MSD cell line described.

Figure 1:
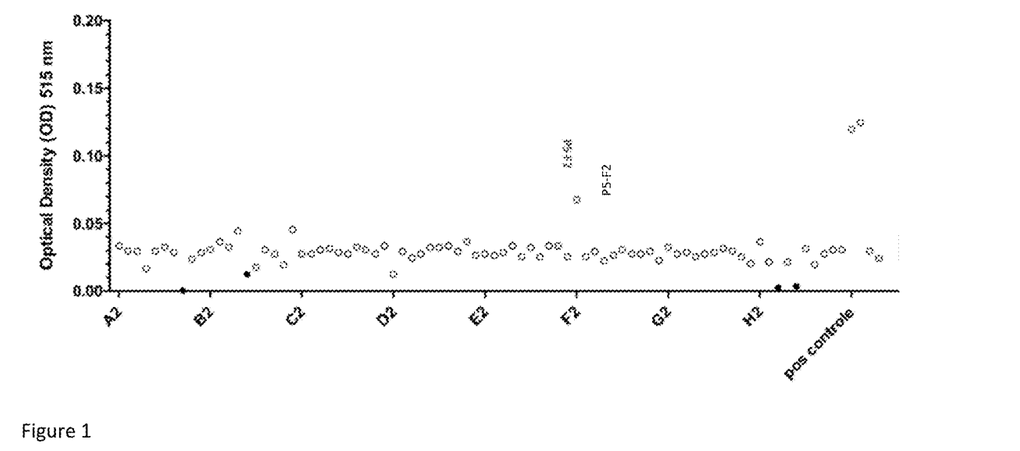
In FIG. 1, the results of the primary screening is shown.

As shown in FIG. 1 inter alia tazarotene (P5-F2), a compound of the class of the third generation retinoids, demonstrates an activity to increase the arylsulfatase A activity in MSD cells.

Figure 2A:
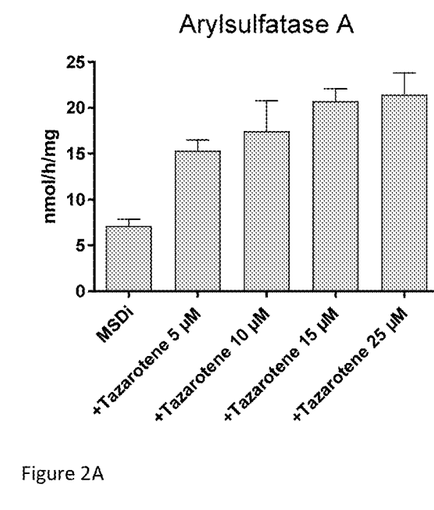
FIG. 2A-C are the results of 3d incubation with tazarotene on immortalized MSD fibroblasts.
Figure 2B:
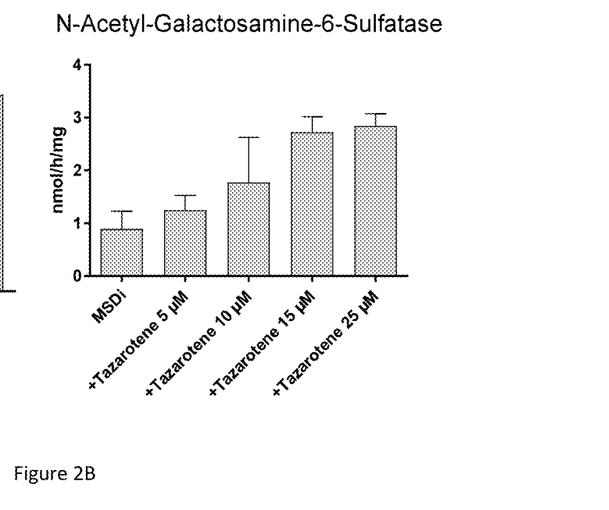
Figure 2C:
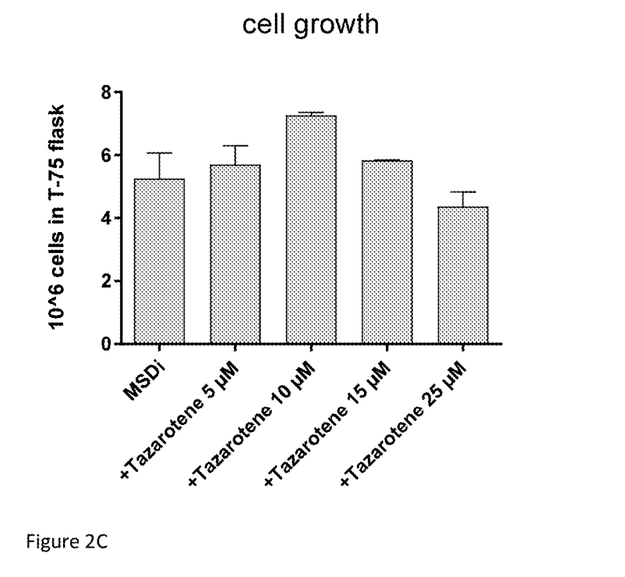

Based on the initial screening test, a dose dependent activity of the arylsulfatase A as well as of the N-acetyl-galactosamine-6-sulfatase activity over a period of three days was screened (FIG. 2). As demonstrated, a dose dependent increase of the activity can be shown. Further, the influence of tazarotene on cell growth has been screened. No significant influence is shown with beta-hexoaminidase A and B as control.

Figure 3A:
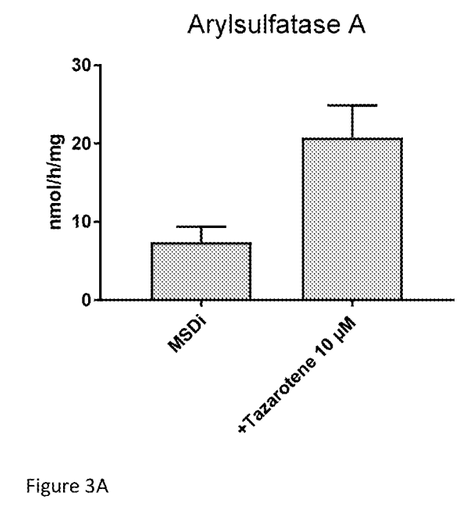
FIG. 3A-D are the results of 6d incubation with tazarotene on immortalized MSD fibroblasts.
Figure 3B:
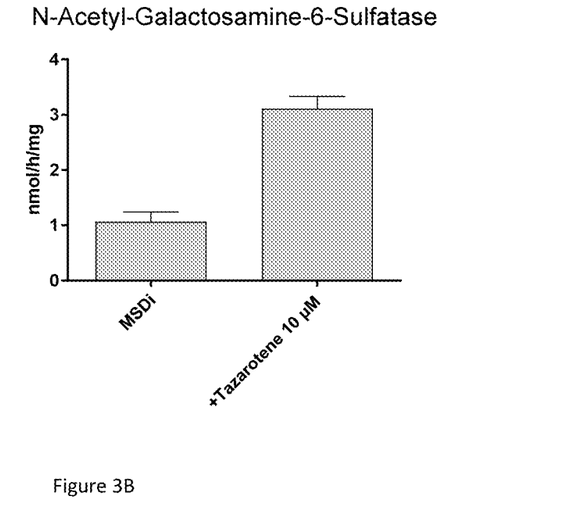
Figure 3C:
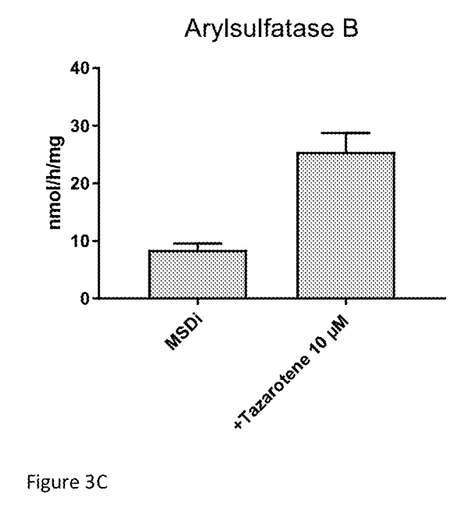
Figure 3D:
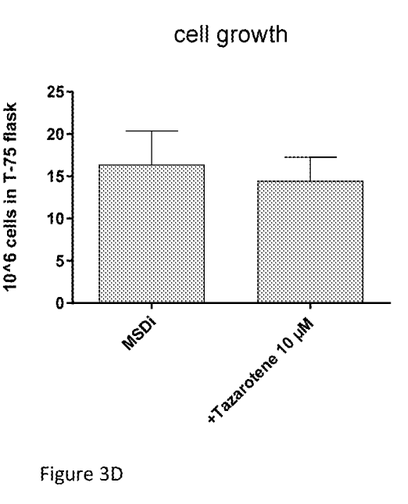

Based on the experiments, the final concentration of 10 μM tazarotene for a treatment time of six days chosen whereby the active ingredient was substituted every three days. After three days, the activity of arylsulfatase A was increased about 2.6 fold while after six days the activity was increased about 2.8 fold, see FIGS. 2A and 3A. The same effects can be shown on N-acetyl-galactosamine-6-sulfatase and aryl-sulfatase B while the cell growth was not significantly influenced (see FIGS. 2 and 3).

Figure 4A:
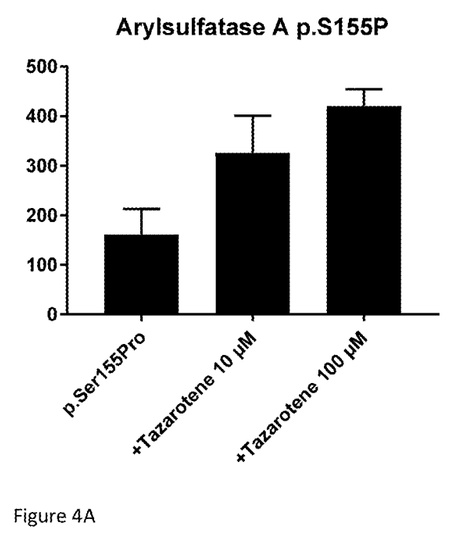
FIG. 4A-C show the results of 3d incubation with tazarotene on primary MSD fibroblasts.
Figure 4B:
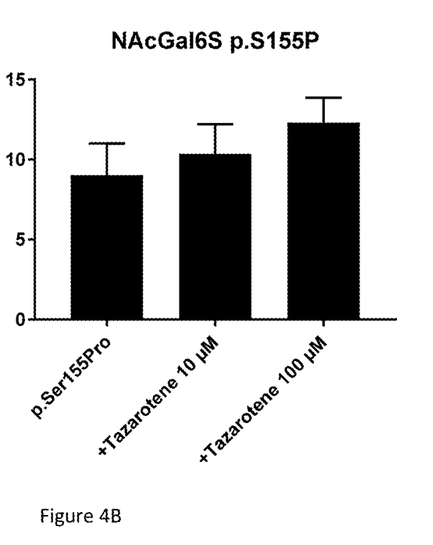
Figure 4C:
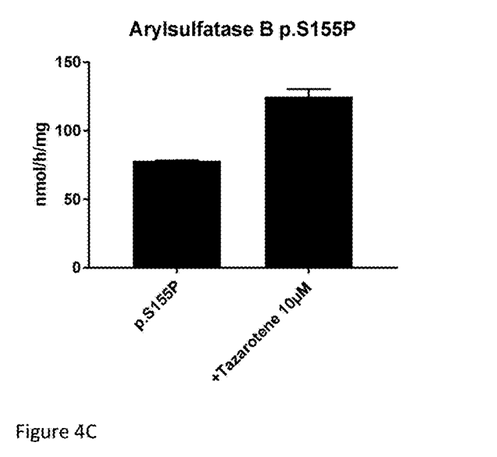

To exclude any effects due to the immortality of the MSDi cells, the experiments were repeated with cell lines of primary fibroblasts obtained from MSD patients. That is, the cell line, from which the immortalized MSD cell line was generated. This cell line has a homozygous SUMF-1 mutation P.S115P in the SUMF 1 gene. After treating six days with tazarotene in concentrations of 10 and 100 μM, respectively, the activity of the aryl-sulfatase A was increased 2.0 fold (10 μM) and 2.6 fold (100 μM), respectively, the increase in N-acetyl-galactosamine-6-sulfatase activity was 1.2 fold and 1.4 fold, respectively, see FIGS. 4A and B. In addition, the activity on arylsulfatase B was determined showing a 1.6 fold increased with 10 μM tazarotene. The cell growth was slowed, while the activity of the control enzyme, the beta-hexoaminidase A was unchanged.

Figure 5A:
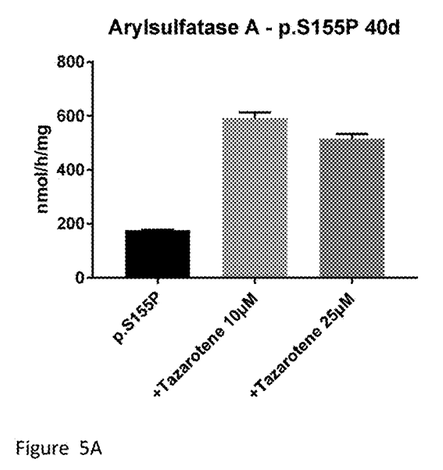
FIG. 5A-C demonstrates the effect of tazarotene on cells with different mutations after 40d incubation.
Figure 5B:
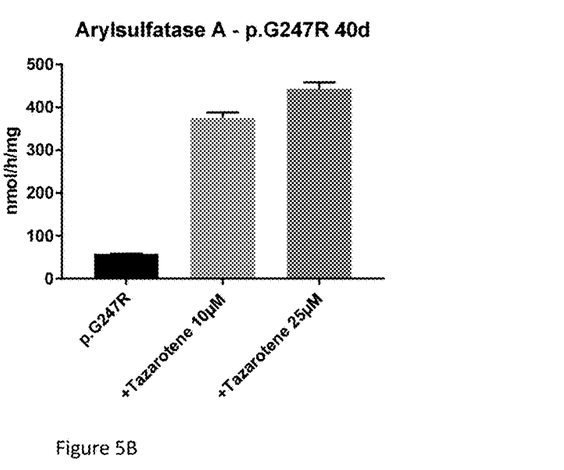
Figure 5C:
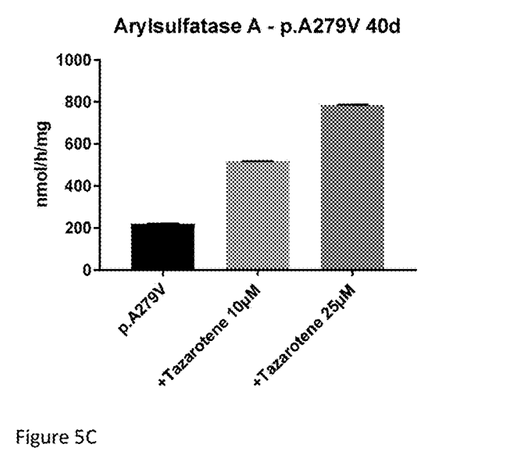

About 50 different mutations in the SUMF-1 gene of MSD patients are known. To exclude a mutation specific effect of the tazarotene treatment, the inventors treated different fibroblasts cell lines obtained from patients with different homozygous SUMF-1 mutations for six days with 10 and 100-μM tazarotene respectively. The increase in activity on the tested sulfatase in all MSD cell lines was independent from the mutation (data not shown). Treatment of the cell lines over 40 days whereby tazarotene was changed every three days and cells were divided after confluence, resulting an increase in arylsulfatase A activity, see FIG. 5.

Figure 6:
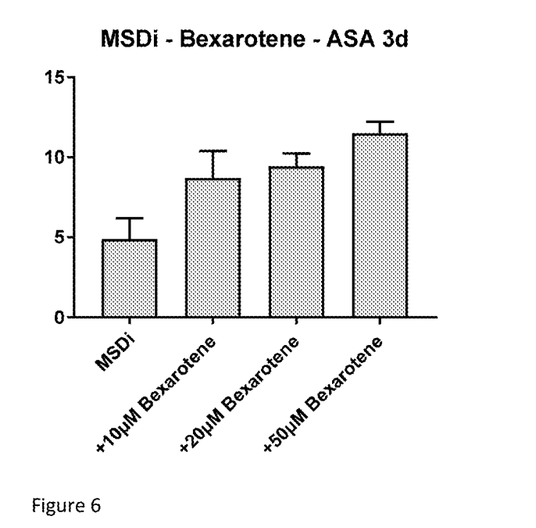
Figure 7A:
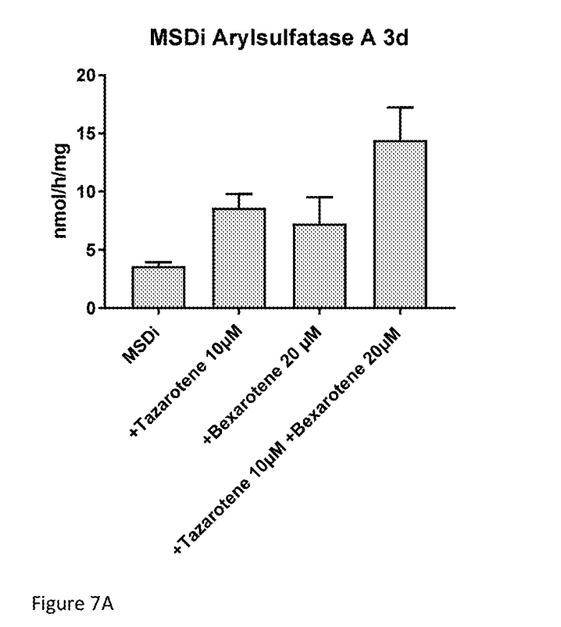
FIG. 7A-B demonstrates the superiority of combining tazarotene with Bexarotene.
Figure 7B:
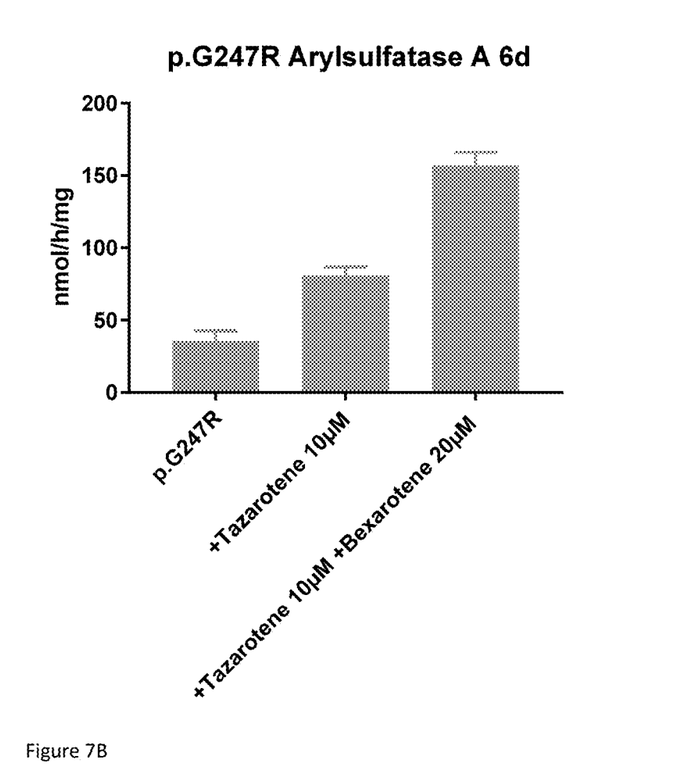

Further compounds were tested including bexarotene. As shown in FIG. 6 bexarotene demonstrates an effect on the aryl sulfatase activity. Taking the above results into account, in a next experiment the immortalized MSDi cells were treated with a combination of tazarotene and bexarotene. As shown in FIG. 7, the increase in the activity of arylsulfatase A after three days treatment compared to the untreated control was 4.0 fold with the combination of tazarotene and bexarotene while the results of single treatment are about 2.4 fold and 2.0 fold.

Also in non-immortalized MSD fibroblast cell lines, the combination of both after treating with the combination for six days, the increase and the arylsulfase A activity was remarkable, see FIG. 9, showing that single administration of tazarotene was results in an increase of 2.3 fold while a combination results an increase of 4.4 fold.

Moreover, a decrease in the lysosomal size in treated cells can be observed compare to untreated cells (data not shown).

As demonstrated in the example, tazarotene and bexarotene as representators of retinoids are suitable for the treatment of MSD, a disease for which present no curative treatment is available. In particular, a combination of these two retinoids as representors of retinoids of the third generation demonstrate a successful approach for treatment of MSD.

The results demonstrate an increase in the activity of deficient sulfatase as well as a decrease of the size of lysosomes due to the reduction of substrates accumulated therein. Thus, these data demonstrates that it is possible to influence the pathophysiology of MSD on cellular level. In particular, increase of the activity, e.g. on a level of 50% of the normal activity, is achievable, thus, correcting the pathomechanism of the disease. There is knowledge on other lysosomal disorders that an increase of residual activity by even less than 10% alleviates disease in patients.

The invention claimed is:

1. A method for treating an individual suffering from multiple sulfatase deficiency comprising the step of administering at least once a therapeutically effective amount of at least one retinoid to said individual, wherein the at least one retinoid is a third-generation retinoid that increases arylsulfatase A activity in cells, and wherein the at least one retinoid is:

a compound of formula I where X is S or O; R is hydrogen or C1-C4 alkyl; $R_2$ is methyl;

A is pyridyl; n is 0-2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a C1-C4 alkylphenol, or an amide or a mono or disubstituted amide thereof, the substituents on the amide being selected from a group consisting of saturated aliphatic radicals of ten or fewer carbon atoms, cyclic or saturated aliphatic cyclic radicals of 5 to 10 carbon atoms, and phenyl or C1-C4 alkylphenyl radicals, or the at least one retinoid is a compound of general formula II wherein $R_1$, $R_2$, $R_3$ and $R_4$ each independently represent hydrogen or lower alkyl having 1-4 carbon atoms;

Y represents C, O, S, N;

$R_5$ represents hydrogen, a lower alkyl having 1-4 carbon atoms, halogen, or nitro;

$R_6$ represents hydrogen, a lower alkyl having 1-4 carbons, halogen or nitro;

$R_7$ and $R_8$ each independently represent hydrogen or lower alkyl having 1-4 carbon atoms;

$R_9$ is COOH, CHO, CH$_2$OH, CONH$_2$, COSH, COOR$_{10}$, COSR$_{10}$, CONHR$_{10}$ with $R_{10}$ represents a lower alkyl having 1-4 carbons or a pharmaceutically acceptable salt thereof.

2. The method according to claim 1 wherein said therapeutically effective amount of at least one retinoid is administered to said individual at least twice in a given time period, wherein the given time period is a day, 3 days, 6 days, or 40 days.

3. The method according to claim 1 where X is S, R is hydrogen, and n is 0 or 1.

4. The method according to claim 3 wherein the compound is ethyl 6-(2-(4,4-dimethylthiochroman-6-yl)ethynyl) nicotinate or a pharmaceutically acceptable salt thereof.

5. The method for treating an individual suffering from multiple sulfatase deficiency according to claim 1 wherein the at least one retinoid is 4-[1-(5,6,7,8-tetrahydro-3,5,5,8,8-pentamethyl-2-naphthalenyl)ethenyl]benzoic acid or a pharmaceutically acceptable salt thereof.

6. The method for treating an individual suffering from multiple sulfatase deficiency according to claim 1, comprising the step of administering a therapeutically effective amount of a combination of ethyl 6-(2-(4,4-dimethylthiochroman-6-yl)ethynyl)nicotinate or a pharmaceutically acceptable salt thereof and 4-[1-(5,6,7,8-tetrahydro-3,5,5,8,8-pentamethyl-2-naphthalenyl)ethenyl]benzoic acid or a pharmaceutically acceptable salt thereof.

\* \* \* \* \*